(12) United States Patent
Machiyama et al.

(10) Patent No.: US 6,369,337 B1
(45) Date of Patent: Apr. 9, 2002

(54) SEPARABLE FAT SCALE

(75) Inventors: Toshihiko Machiyama; Hiroki Tanaka, both of Osaka (JP)

(73) Assignee: Misaki, Inc., Osaka (JP)

( * ) Notice: Subject to any disclaimer, the term of this patent is extended or adjusted under 35 U.S.C. 154(b) by 0 days.

(21) Appl. No.: 09/598,176

(22) Filed: Jun. 21, 2000

(51) Int. Cl.[7] .................... A61B 5/05; G01G 23/00
(52) U.S. Cl. ........................ 177/25.13; 177/25.16; 177/245; 600/547
(58) Field of Search .................... 177/25.13, 25.16, 177/245; 600/547

(56) References Cited

U.S. PATENT DOCUMENTS

| | | | | |
|---|---|---|---|---|
| 5,415,176 A | * | 5/1995 | Sato et al. | 177/245 |
| 5,579,782 A | * | 12/1996 | Masuo | 600/547 |
| 5,611,351 A | * | 3/1997 | Sato et al. | 600/547 |
| 6,088,615 A | * | 7/2000 | Masuo | 600/547 |
| 6,208,890 B1 | * | 3/2001 | Sarrazin et al. | 600/547 |
| 6,256,532 B1 | * | 7/2001 | Cha | 600/547 |
| 6,280,396 B1 | * | 8/2001 | Clark | 600/547 |

FOREIGN PATENT DOCUMENTS

JP           5-49050        7/1993

OTHER PUBLICATIONS

U.S. Patent Application Publication #US2001/0007055 A1, Yoshinori Fukuda, Tanita Corp., Jul. 5, 2001.*

* cited by examiner

*Primary Examiner*—Randy W. Gibson
(74) *Attorney, Agent, or Firm*—Wenderoth, Lind & Ponack, L.L.P.

(57) ABSTRACT

Disclosed is a separable fat scale including a body weight measuring part for detecting a body weight of a person under test who mounts a weighing platform; electrode parts having thereon at least a pair of electrodes to electrically contact soles of feet of the person under test and formed separately from the weighing platform; an impedance measuring part for measuring impedance of the person under test through his/her soles contacting the electrodes; an input part for inputting personal data including information about physical characteristics of the person under test such as sexuality, age and body height; an arithmetic part for calculating a proportion of body fat in the body of the person under test and/or weight of the body fat under impedance signals obtained from the impedance measuring part, load signals obtained from the body weight measuring part and the personal data input; and a data output part for outputting the calculated proportion of body fat in the body and/or weight of the body fat, wherein the electrode parts are separated into a right-foot-use electrode part and a left-foot-use electrode part to be separately arranged.

18 Claims, 4 Drawing Sheets

SEPARABLE FAT SCALE

BACKGROUND OF THE INVENTION

1. Field of the Invention

This invention relates to a device for measuring a proportion of body fat and its weight as well as measuring one body weight, for health management or monitoring.

2. Description of the Prior Art

Technologies for measuring weight of body fat contained in one body by measuring weight and impedance of his/her body have been proposed.

For example, Japanese Patent Publication No. Hei 5(1993)-49050 discloses a body fat scale comprising a weighing platform for weighing a body weight; a body weight measuring part for converting electric signals from the weighing platform into body weight signals; and two feet use electrodes which are electrically connected to an impedance measuring part and are adapted to contact with soles of one feet to be measured, respectively. The two electrodes are integrally built in the weighing platform in such a manner as to be electrically insulated from each other.

This body fat scale is designed to incorporate the electrodes in a surface of the weighing platform so that with one simple mounting the weighing platform with one bare feet, the one body weight and impedance can both automatically measured.

It is also designed to have a key-input part for additionally entering therein personal information, such as age and sexuality, necessary for accurate calculation of weight of body fat from the body weight and impedance of one body.

In this conventional body fat scale, the two electrodes, i.e., the right-foot-use electrode and the left-foot-use electrode, are fixedly arranged on and integrated with the weighing platform. With this arrangement, there is a limited space between the two electrodes and, accordingly, inner thighs of a user are subject to contact with each other, depending on the user physical constitution.

When the inner thighs contact with each other during the measurement of impedance of one body, the route for electric current to pass from the right-foot-use electrode to the left-foot-use electrode by way of one body is short-circuited at the contacting part of the thighs. As a result of this, two routes, i.e., a first route for electric current to pass through the one body and a second route as short-circuited at his/her thighs, are presented in the form of a parallel circuit, which causes an error by rendering the impedance lower than the first route only. For this reason, with this conventional arrangement of two built-in electrodes being arranged with a limited space therebetween, the error sometimes becomes some tens of percents.

It has been proven that improved accuracy of measurement of the impedance is provided by a standing posture with one's right and left feet spread out to some extent. This seems to be because, since the standing posture with one both feet spreading out produces a balanced posture with little stagger and thus produces little variation in pressure at the joints, whereby the impedance is stabilized and thus the measurement of the body fat is also stabilized.

Thus, the impedance should desirably be measured in the standing posture with the right and left feet straddling or spread out to some extent. The two built-in electrodes arrangement has the disadvantage, however, that the spreading of the space between the two electrodes will involve the upsizing of the entire device and thus the increasing of storage space for the scale to use at home, thereby resulting in the disadvantage of difficulty of use.

In addition, the conventional arrangement in which the two electrodes are built in the weighing platform has the following disadvantages in repair and replacement. When deterioration, damage or failure of the electrode surface occurs, it is hard to replace only the damaged electrode with a new one. Also, in the state in which the electrodes are removed from the scale, the scale can no longer be used as a weighing machine.

SUMMARY OF THE INVENTION

The present invention is made with the aim to provide improved accuracy of measurement of body fat in a separable fat scale in which a body weight measuring part and an electrode part are separately arranged.

The present invention provides a separable fat scale comprising a body weight measuring part for detecting a body weight of a person under test who mounts a weighing platform; electrode parts having thereon at least a pair of electrodes to electrically contact with soles of feet of the person under test and formed separately from the weighing platform; an impedance measuring part for measuring impedance of the person under test through his/her soles contacting with the electrodes; an input part for inputting personal data including information about physical characteristics of the person under test such as sexuality, age and body height; an arithmetic part for calculating a proportion of body fat in the body of the person under test and/or weight of the body fat under impedance signals obtained from the impedance measuring part, load signals obtained from the body weight measuring part and the personal data input; and a data output part for outputting the calculated proportion of body fat in the body and/or weight of the body fat, wherein the electrode parts are separated into a right-foot-use electrode part and a left-foot-use electrode part to be separately arranged. With this arrangement, the electrode parts can be spaced apart so that inner thighs of the person under test can be prevented from contacting each other, thus producing the effect of providing improved accuracy of measurement of the body fat.

The physical characteristics which maybe selectively input as the personal data include not only sexuality, age, body height and crotch height of the person under test but also a length between outstretched hands, a length from navel to sole, girth of an arm, girth of thighs, girth of lower thighs, girth of a breast, girth of an abdominal part, girth of a lumbar part, and sitting height. In accordance with this personal information, some components, such as coefficients of the conversion equation in the arithmetic part can be modified to calculate the proportion of body fat with further accuracy.

The input part and the data output part may selectively be arranged on the body weight measuring part side or on the electrode part side.

Also, the data output part maybe realized by visual information output means (display panel and the like) or audible information output means (synthetic voice output device and the like).

DETAILED DESCRIPTION OF THE PREFERRED EMBODIMENTS

The present invention will be described in detail by way of illustrative examples with reference to the accompanying drawings.

(Overall Arrangement)

Figure 1:
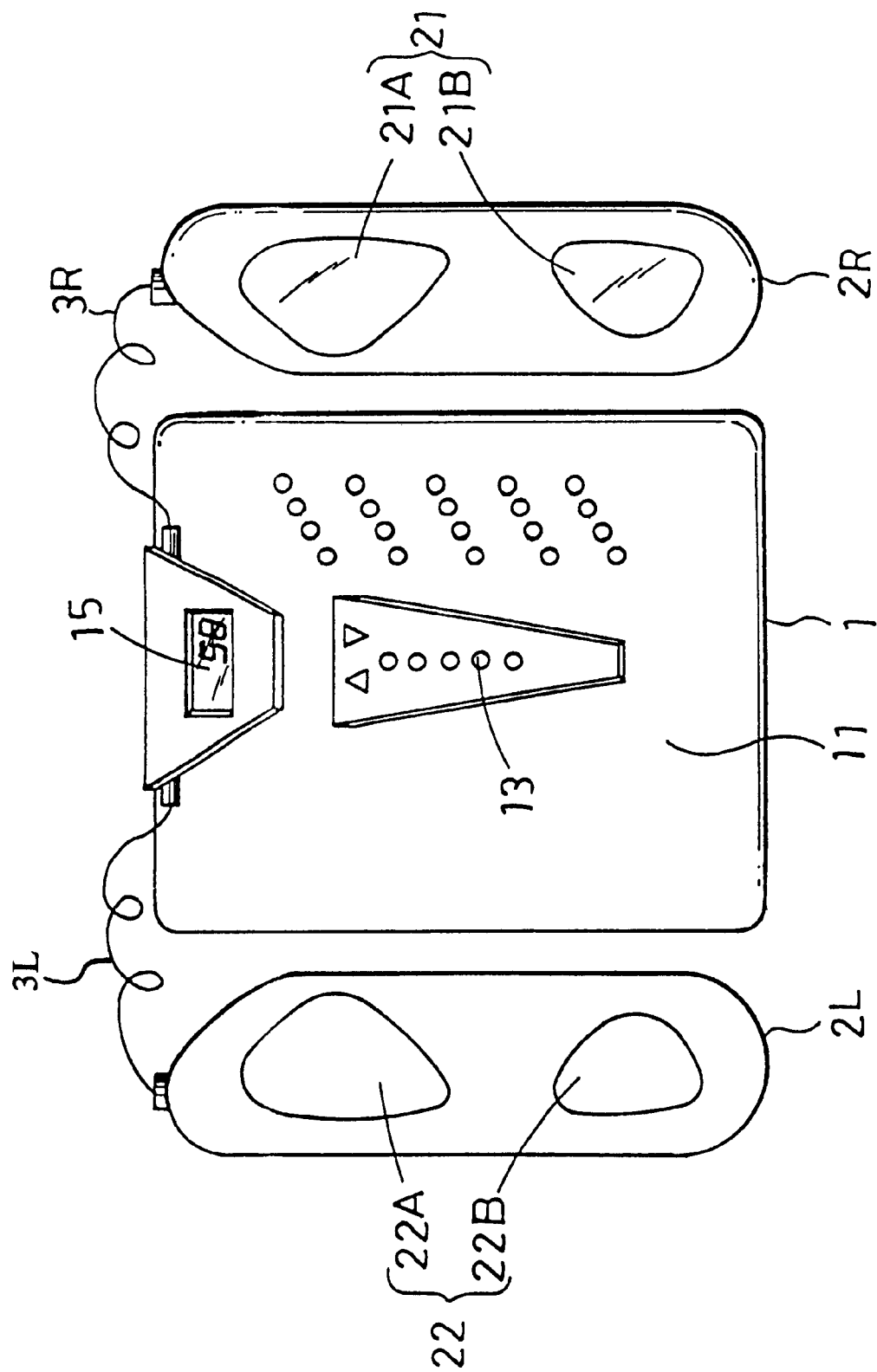
FIG. 1 is a perspective view showing an embodiment of a separable fat scale according to the present invention.

Referring to FIG. 1, which shows a perspective view of a separable fat scale of an embodiment according to the present invention, reference numeral 1 designates a body weight measuring part; 2R designates a right-foot-use electrode part separately arranged from the body weight measuring part; and 2L designates a left-foot-use electrode part separately arranged from the body weight measuring part and the right-foot-use electrode part 2R.

The right-foot-use electrode part 2R and the left-foot-use electrode part 2L are electrically connected to the body weight measuring part 1 via cords 3R, 3L. Each of the cords 3R, 3L is provided with a detachable connector.

The body weight measuring part 1 houses therein a load cell 12 for detecting a body weight of a person under test who mounts a weighing platform 11 and outputting load signals, an input part 13 for entering personal data, such as sexuality, age and body height of a person under test, an arithmetic part 14 for calculating a proportion of body fat in his/her body and a weight of the body fat and a display part 15 for displaying the calculated values including the proportion of body fat, weight thereof and body weight.

The body weight measuring part 1 has small anti-slip projections and depressions formed on its surface at a foot mounting part thereof.

Arranged on the surface of the right-foot-use electrode part 2R is a right-foot-use electrode 21 to be electrically contacted with a sole of the right foot of the person under test. Arranged on the surface of the left foot use electrode part 2L is a left foot use electrode 22 to be electrically contacted with a sole of the left foot of the person under test.

These electrodes 21, 22 are connected with the body weight measuring part 1 via the cords 3R, 3L.

(Circuitry of Body Weight Measuring Part)

Figure 2:
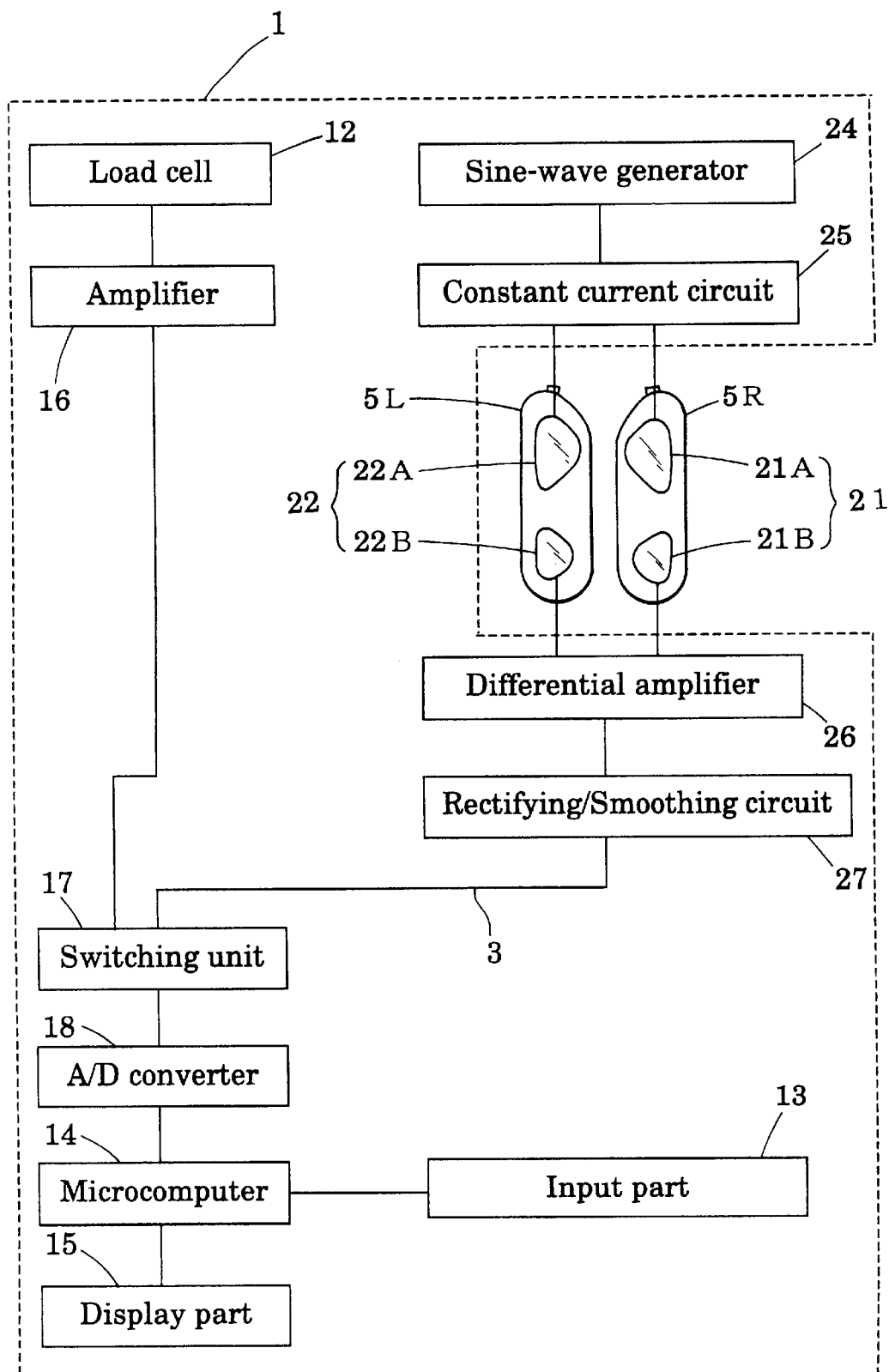
FIG. 2 is a circuitry diagram of the separable fat scale of FIG. 1.

Referring now to FIG. 2, which shows a circuitry diagram of the separable fat scale of the present invention, the body weight signals obtained in the load cell 12 are input to an amplifier 16 so as to be amplified. Then, the amplified signals are input to a switching unit 17.

Once the switching is made to the body weight measuring mode in the switching unit 17, the body weight signals fed from the amplifier are converted into digital signals by an A D converter 18 and then are fed to the arithmetic part 14 using a microcomputer. In the arithmetic part, those signals are converted into body weight display data and are displayed in the display part 15. At this time, the body weight data is stored in the memory of the arithmetic part 14.

(Circuitry around Electrode Part)

In FIG. 2, in constant current circuit 25, sine-wave signals generated in a sine-wave generator 24 are applied to the soles of the both feet of the person under test as constant current sine-wave signals through applying electrodes 21A, 22A.

The sine-wave signals detected from detecting electrodes 21B, 22B are amplified in a differential amplifier 26 and further are converted into DC signals in a rectifying/smoothing circuit 27. Then, the signals thus converted are fed to the switching unit 17 of the body weight measuring part 1 through a cable 3.

Once the switching is made to the body fat scale mode in the switching unit 17, the DC signals from the electrode part are converted into digital signals by the AD converter 18 and then are fed to the arithmetic part 14 using the microcomputer.

The arithmetic part 14 forms an impedance measuring part as well in cooperation with the sine-wave generator 24, the constant current circuit 25, the differential amplifier 26 and the rectifying/smoothing circuit 27.

(Operation of Arithmetic Part)

In the arithmetic part 14, the impedance of body between the detecting electrodes 21B, 22B are calculated by a four-terminal electrode process, first. The measured impedance, the body weight data obtained from the signals of the load cell 12 and the personal data such as sexuality and body height are used to calculate the proportion of body fat, the weight of the body fat and the degree of obesity under the following conversion equation. Then, all data on the body weight, proportion of body fat, weight of the body fat and degree of obesity or any selectively specified data therefrom are displayed in the display part 15. The proportion of body fat and the degree of obesity are graphically displayed for good visibility.

In the body fat scale mode, either of the impedance and the body weight may be measured first or may be concurrently measured. In the body fat scale mode, the arithmetic operation is on standby and is not performed until the measurement of the impedance and the measurement of the body weight are completed. If the both measurements are not completed even after more time than the preset standby time passes, then the reset is triggered. Only one of them may be measured and the other may be input from a keyboard of the input part.

(Conversion Equation)

The body density (BD) is given by:

$$BD = a - b \times W \times Z/H2$$

where a and b are coefficients;
W is a body weight (Kg) of a person under test;
H is a body height (cm); and
Z is measured impedance ($\Omega$).

The proportion of body fat (% F) is given by:

$$\% F = (c/BD - d) \times 100$$

where c and d are coefficients.

The weight of body fat (BF) is given by:

$$BF\ (Kg) = W \times \% F/100.$$

As a substitute for the arithmetic expressions as given above, an alternative arithmetic expression for calculating the proportion of body fat and the weight of the body fat with further accuracy may be determined by selectively using any data on the information about physical characteristics of a person under test. For example, in the case where the data on not only a body height but also a crotch height are used, the arithmetic equation or expression is additionally determined.

When the memory of the arithmetic part 14 is increased in capacity and also is formed of a nonvolatile memory so as to include the capabilities of storing and holding personal data of a person under test, the troublesome labor of inputting each measurement can be saved. Also, when the arithmetic part 14 is designed to include the calendar capability, changes in the body weight and body fat of the person under test can be stored together with the data on date and also those changes can be graphically represented.

While in the aforesaid description, no reference is given to discrimination against the person under test, when this scale is used by a number of persons, the personal data of every person and the measured data thereof may preferably be stored on a individual basis so that they can easily be called with a calling key so as to be used for arithmetic operations and display.

The electrode parts 2R, 2L thus separated normally take the standard form of being located at both lateral sides of the body weight measuring part 1.

In use, a person under test mounts the weight measuring part 1 at the center to capture the body weight data, first. Then, he/she mounts the electrode parts 2R, 2L to capture the impedance data. These steps can be done in reverse order. In any event, when both data are captured within a predetermined time or when the body weight data is entered from the input part, the arithmetic operation is started to display the body weight and the proportion of body fat or the weight of the body fat.

A buzzer housed may be used to emit a sound when the scale prompts him/her to mount the electrode parts, requests him/her to input the concerned data, recognizes the data, or performs the display in the course of or at the completion of arithmetic operation.

When he/she mounts the electrode parts 2R, 2L thus arranged to measure the impedance, he/she takes a standing posture with his/her legs apart across the body weight measuring part 1. Accordingly, the inner thighs can be prevented from contacting each other, thus providing improved accuracy of the measurement of impedance or improved accuracy of measurement of body fat.

When both electrode parts are spaced excessively, children in particular will take an unstable standing posture. Accordingly, both electrode parts may be spaced with any adequate interval at a location before the body weight measuring part.

Thus, the arrangement of the right and left electrode parts being separately arranged enables the two electrode parts to be spaced with any adequate interval for the user physical constitution within the range that the inner thighs do not contact each other. This enables accurate measurement of the body fat in an optimum posture, irrespective of the physical constitution of a person under test or of a user.

The body weight measuring part 1 can be used by itself as a weighing machine without connecting the right and left electrode parts 2R, 2L thereto.

Also, the right and left electrode parts 2R, 2L may be sold separately from the body weight measuring part 1 so that it may be added thereto at a future date.

As seen from the above, the arrangement of the electrode parts 2R, 2L being separated from the body weight measuring part 1 can provide a variety of usage and marketing techniques.

Also, the arrangement of the right and left electrode parts being separated from each other enables only either of the two electrode parts to be simply replaced for repair, thus providing no wastefulness and producing savings.

Also, even in the state in which the electrode parts are detached from the scale, the remainder can at least be used as the weighing machine.

Figure 3:
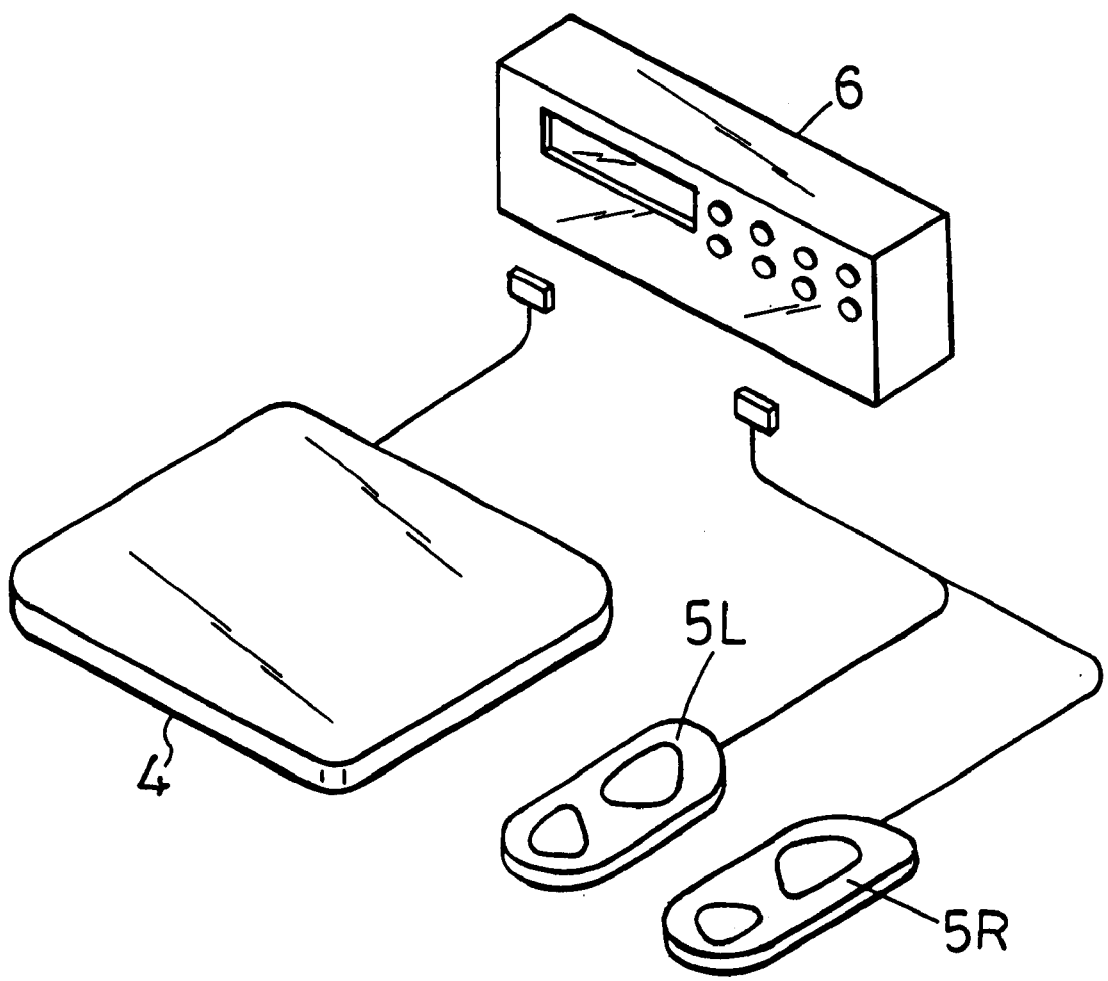
FIG. 3 is a perspective view of another embodiment of the present invention.

Further, as shown in FIG. 3, an operating part 6 including at least the input part and the display part may be separated from the weighing platform 4 and the electrode parts 5R, 5L so that the operating part 6 can be placed in a place easily viewable and easy to operate.

Figure 4:
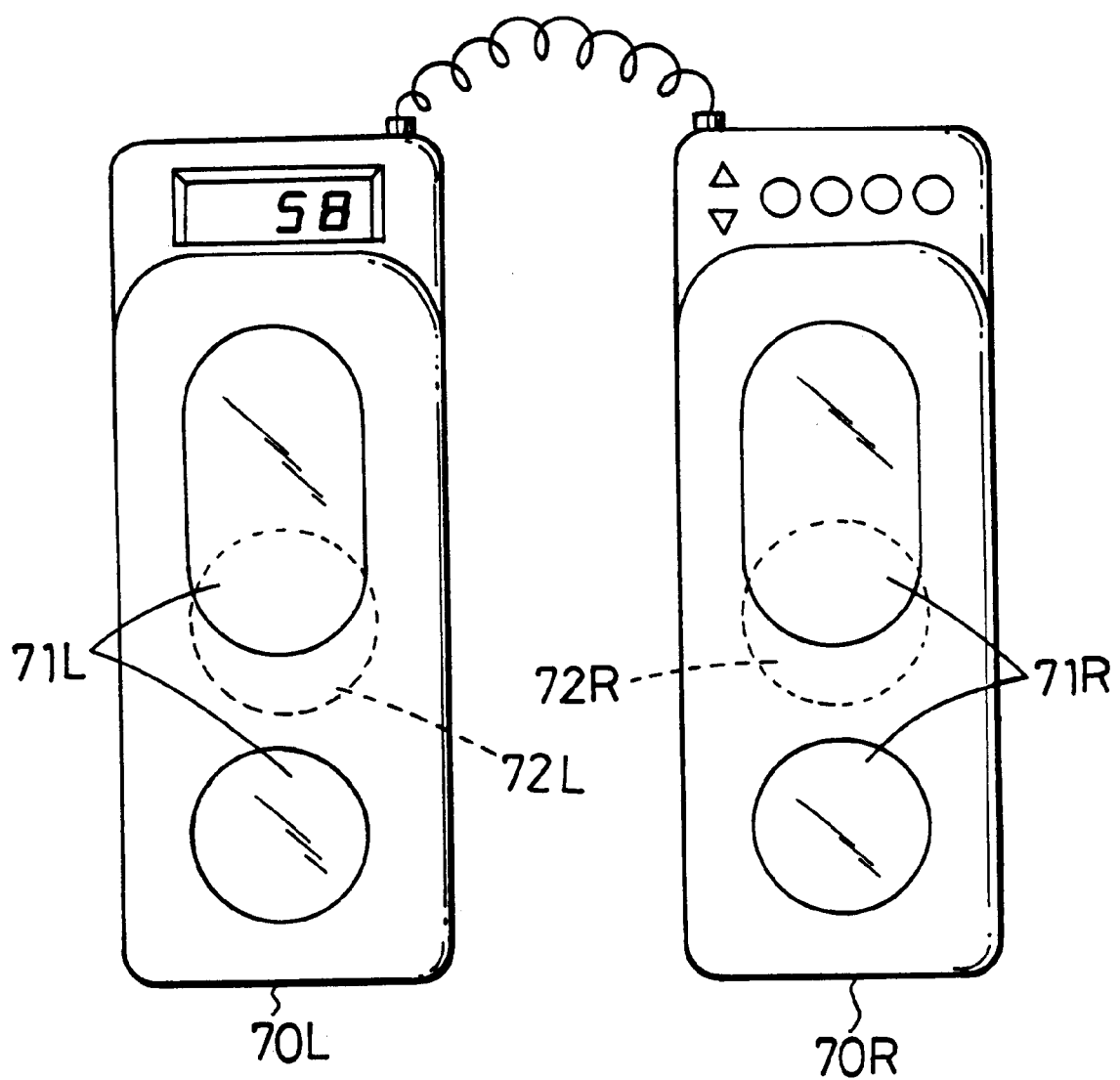
FIG. 4 is a plan view of a further embodiment of the present invention.

While the body fat scale illustrated above is arranged centered on the body weight measuring part, another arrangement of FIG. 4 may be adopted which comprises a right-foot-use measuring part 70R having an electrode part 71R and a body weight sensor 72R and a left-foot-use measuring part 70L having an electrode part 71L and a body weight sensor 72L.

In this variation, the impedance measuring part, the input part, the arithmetic part and the data output part may be housed in either of the measuring parts or may be housed in a separately independent operating part.

As for the operation for the measurement of impedance, this variation is identical to the aforesaid arrangement and, accordingly, the description thereon is omitted. As for the measurement of body weight, this variation is only different from the aforesaid arrangement in that the total body weight is obtained by addition of signals of the right and left body-weight sensors 72R, 72L and is identical in the other aspects. Accordingly, the description thereon is omitted.

With this formation, since the loads applied to both feet can be separately detected by the right and left body-weight sensors, when an extremely unbalanced load is applied to either foot, the user can be prompted to mount in a well-balanced posture by producing a warning. The mounting in the well-balanced posture can produce a uniform contact between the electrodes and the soles of the feet, thus enabling a further accurate measurement of the impedance.

Instead of the cord used to detachably connect the body weight measuring part and the right and left electrode parts, wireless communication means such as infrared light, weak electric waves and supersonic waves may be used. Also, the electric power may be supplied together with data communication by use of electromagnetic coupling.

Further, solar panels may be arranged on the electrode parts. The scale can have the capabilities of detecting the mounting to the weighing platform, turning on power for the arithmetic part and the display part and automatically turning off power after a preset time passes after the dismounting from the weighing platform.

In addition, the data on e.g. the proportion of body fat may be output as audible information in a synthetic voice in order to call "need care" to the user attention when the proportion of body fat exceeds a preset value or to offer encouragement of "one more push" to a person on a diet when the proportion of body fat falls toward a targeted value. This enables the scale to be effectively used even by persons with auditory difficulties.

What is claimed is:

1. A scale comprising:
    a right-foot-use electrode part including an electrode to electrically contact the sole of the right foot of a person;
    a left-foot-use electrode part including an electrode to electrically contact the sole of the left foot of the person; and
    an impedance measuring part, connected to said right-foot-use electrode part and said left-foot-use electrode part, for measuring impedance of the person via the sole of the right foot of the person being in contact with said electrode of said right-foot-use electrode part and the sole of the left foot of the person being in contact with said electrode of said left-foot-use electrode part,
    wherein said right-foot-use electrode part and said left-foot-use electrode part are movably associated with each other such that a distance between said right-foot-use electrode part and said left-foot-use electrode part can be adjusted.

2. The scale according to claim 1, further comprising a body weight measuring part, including a weighing platform for detecting a body weight of the person, wherein said right-foot-use electrode part and said left-foot-use electrode part are movably associated with each other by being independently movable relative to said weighing platform.

3. The scale according to claim 2, further comprising an input part for inputting personal data about the person including gender of the person, age of the person and height of the person.

4. The scale according to claim 3, further comprising an arithmetic part for calculating at least one of proportion of body fat of the person and weight of the body fat of the person from impedance signals received from said impedance measuring part, load signals received from said body weight measuring part, and the inputted personal data.

5. The scale according to claim 4, further comprising a data output part for outputting at least one of the calculated proportion of body fat of the person and the calculated weight of the body fat of the person.

6. The scale according to claim 5, wherein said right-foot-use electrode part and said left-foot-use electrode part are each independently movable relative to said weighing platform by being attached to said body weight measuring part via a flexible cord.

7. The scale according to claim 6, wherein said body weight measuring part includes a load cell for detecting the body weight of the person, and said body weight measuring part houses said load cell, said input part, said arithmetic part and said data output part.

8. The scale according to claim 5, wherein said body weight measuring part includes a load cell for detecting the body weight of the person, and said body weight measuring part houses said load cell, said input part, said arithmetic part and said data output part.

9. The scale according to claim 5, wherein said body weight measuring part includes a load cell for detecting the body weight of the person, said body weight measuring part houses said load cell and said arithmetic part, and said input part and said and said data output part are housed in a separate operating part.

10. The scale according to claim 2, wherein said right-foot-use electrode part and said left-foot-use electrode part are each independently movable relative to said weighing platform by being attached to said body weight measuring part via a flexible cord.

11. The scale according to claim 1, further comprising a body weight sensor provided in each of said right-foot-use electrode part and said left-foot-use electrode part.

12. The scale according to claim 11, further comprising an input part for inputting personal data about the person including gender of the person, age of the person and height of the person.

13. The scale according to claim 12, further comprising an arithmetic part for calculating at least one of proportion of body fat of the person and weight of the body fat of the person from impedance signals received from said impedance measuring part, signals received from said body weight sensors, and the inputted personal data.

14. The scale according to claim 13, further comprising a data output part for outputting at least one of the calculated proportion of body fat of the person and the calculated weight of the body fat of the person.

15. The scale according to claim 14, wherein said right-foot-use electrode part and said left-foot-use electrode part are movably associated with each other by being interconnected via a flexible cord.

16. The scale according to claim 15, wherein said impedance measuring part, said input part, said arithmetic part and said data output part are each housed in either one of said right-foot-use electrode part and said left-foot-use electrode part.

17. The scale according to claim 1, wherein said right-foot-use electrode part and said left-foot-use electrode part are movably associated with each other by being interconnected via a flexible cord.

18. The scale according to claim 17, further comprising a body weight sensor provided in each of said right-foot-use electrode part and said left-foot-use electrode part.

* * * * *